US006312718B1

(12) United States Patent
Popescu et al.

(10) Patent No.: US 6,312,718 B1
(45) Date of Patent: Nov. 6, 2001

(54) VACCINE FOR B-CELL MALIGNANCIES

(75) Inventors: Mircea C. Popescu, Plainsboro, NJ (US); Larry Kwak; Augusto C. Ochoa, both of Frederick, MD (US); Larry Boni, Monmouth Junction, NJ (US)

(73) Assignee: Biomira USA, Inc., Cranbury, NJ (US)

( * ) Notice: Subject to any disclaimer, the term of this patent is extended or adjusted under 35 U.S.C. 154(b) by 0 days.

(21) Appl. No.: 09/125,376

(22) PCT Filed: Feb. 13, 1997

(86) PCT No.: PCT/US97/02351

§ 371 Date: Oct. 27, 1998

§ 102(e) Date: Oct. 27, 1998

(87) PCT Pub. No.: WO97/29769

PCT Pub. Date: Aug. 21, 1997

Related U.S. Application Data

(60) Provisional application No. 60/011,783, filed on Feb. 16, 1996.

(51) Int. Cl.$^7$ .................................................. A61K 39/395
(52) U.S. Cl. .................. 424/450; 424/130.1; 424/184.1; 424/85.1; 424/277.1
(58) Field of Search ............................ 424/130.1, 184.1, 424/85.1, 277.1, 450

(56) References Cited

U.S. PATENT DOCUMENTS

| | | | |
|---|---|---|---|
| 4,036,945 | 7/1977 | Haber | 424/1 |
| 4,331,647 | 5/1982 | Goldenberg | 424/1 |

OTHER PUBLICATIONS

Chan et al AIDS, 9:223–228 1995.*
George et al J. Immunol. 141:2168–2174, 1988.*
Epstein et al Clin. Exper. Immunol. 53:257–271, 1983.*
Gregoriadis J Drug Targeting 2(5): 351–356, 1994.*
Arthur et al J Virol. 69(5): 3117–3124, 1995.*
T.M. Allen et al., "Pharmacokinetics of stealth versus unconventional liposomes: effect of dose", Biochimica et Biophysica Acta, 1068, (1991) pp. 133–141.
T.M. Allen et al., "Subcutaneous administration of liposomes: a comparison . . . routes of injection", Biochimica et Biophysica Acta., 1150, (1993), pp. 9–16.
S.M. Andrew et al., "Purification and Fragmentation of Antibodies", Current Protocols in Immuno. (1997) pp. 2.7.1–2.7.12.
M.G. Baines et al., "Purification of Immunoglobulin G (IgG)", Methods in Molecular Biology, vol. 10, Immuno. Protocols, 1992, pp. 79–104.
I.A.J.M Bakker–Woudenberg et al., "Liposomes as Carriers of Antimicrobial Agents or . . . Treatment of Infections", Eur. J. Clin. Microbiol. Infect. Dis., vol. 12, Supp. 1, 1993, pp. 61–67.

E. Claassen et al., "The Effect of Elimination of Macrophages on the Tissue Distribution . . . [$^3$H]Thotrexate", Biochema et Biophysica Acta, 802 (1984), pp. 428–434.
D. Colcher et al., "In Vivo Tumor Targeting of a Recombinant Single–Chain Antigen–Binding Protein", J. Nat. Cancer Inst., vol. 82, No. 14, 7/90, pp. 1191–1197.
L. R. Coney et al., "Cloning of a Tumor–associated Antigen: Mov18 and MOv19 Antibodies Recognize a Folate–binding Protein", Cancer Research 51, (11/91) pp. 6125–6132.
J. Fagerberg et al., "Induction of an immune network cascade in cancer patients treated with mono–clonal antibodies (ab$_1$)", Cancer Immunol. Immun. 37 (1993), pp. 264–270.
P.L. Felgner et al., "Lipofection: A highly efficient, lipid–mediated DNA–transfection procedure", Proc. Natl. Acad. Sci, USA, vol. 84, (11/87), pp. 7413–7417.
R.M. Fielding, "Liposomal Drug Delivery", Clin Pharmacokinetics, 21(3): 155–164, 1991.
K.A. Foon, "Chronic Lymphoid Leukemias: Recent Advances in Biology and Therapy", Stem Cells, vol. 13, 1995, pp. 1–21.
H.M. Geysen et al., "Strategies for epitope analysis using peptide synthesis", J. Immunol. Methods, vol. 102 (1987), pp 259–274.
A. Skerra et al., "Assembly of a Functional Immunoglobulin F$_v$ Fragment in *Escherichia coli*", Science, vol. 240, (5/88), pp. 1038–1041.
R. Glockshuber et al., "A comparison of Strategies to Stabilize Immunoglobulin F$_v$–Fragments", Biochemistry, vol. 29, (1990), pp. 1362–1367.
D.M. Goldenberg, "Monoclonal Antibodies in Cancer Detection and Therapy", The Amer. J. of Med., vol. 94, (3/93), pp. 297–312.
J. Haensler et al., "Polyamidoamine Cascade Polymers Mediate Efficient Transfection of Cells in Culture", Bioconjugate Chem., vol. 4, (1993), pp. 372–379.
D. Herlyn et al., "Specific Detection of Anti–Idiotypic Immune Responses in Cancer Patients Treated with Murine Monoclonal Antibody", J. Immunol. Methods, vol. 85, (1985), pp. 27–38.
N.K. Jerne et al., "Recurrent idiotopes and internal images", EMBO Journal, vol. 1, No. 2, (1982) pp. 243–247.
R.C. Kennedy et al., "Antibody to Hepatitis B Virus Induced by Injecting Antibodies to the Idiotype", Science, vol. 223, (3/84), pp. 930–931.
S. Kim, "Liposomes as Carriers of Cancer Chemotherapy", Drugs 46 (4), pp. 618–638.

(List continued on next page.)

Primary Examiner—Geetha P. Bansal
(74) Attorney, Agent, or Firm—Foley & Lardner (57) ABSTRACT

A vaccine comprising a liposome preparation including at least one B-cell malignancy-associated antigen, IL-2, alone or in combination with at least one other cytokine, and at least one type of lipid molecule, is useful in a method of inducing humoral and cellular immune responses against malignant B-cells in a mammal.

17 Claims, 9 Drawing Sheets

OTHER PUBLICATIONS

D.J. King et al., "Expression, purification and characterization of B72.3 Fv fragments", Biochem. J. vol. 290 (1993), pp. 723–729.

M.E. Klegerman et al., "Lymphokines and Monokines", Biotechnology and Pharmacy, (1993), pp. 53–70.

G. Köhler et al., "Continuous cultures of fused cells secreting antibody of predefined specificity", Nature vol. 256, (1975), pp. 495–497.

T.F. Kresina et al., "Antiidiotypic Antibody Vaccine in Muring . . . image of Antigen", J. Clin. Invest. vol. 83, (3/89), pp. 912–920.

J.W. Larrick et al., "PCR Amplification of Antibody Genes", Methods: A companion to Methods in Ezymology, vol. 2, No. 2, (4/91), pp. 106–110.

R.J. Lee et al., "Delivery of Liposomes into Cultured KB Cells via Folate Receptor–mediated Endocytosis", J. Biological Chem., vol. 269, No. 5, (1994), pp. 3198–3204.

M.J. Losman et al., "Baboon anti–idiotype antibodies mimic carcinoembryonic antigen epitope", Int. J. Cancer, vol. 46, (1990), pp. 310–314.

M.J. Losman et al., "Human response against NP–4, a mouse antibody to . . . epitope on the tumor antigen", Proc. Natl. Acad. Sci. USA, vol. 88, (4/81) pp. 3421–3425.

M.J. Losman et al., "Mimicry of a carcinoembryonic antigen . . . anti–idiotype antibody", Int. J. Cancer, vol. 56, (1994), pp. 580–584.

M.K. McNamara et al., "Monoclonal Idiotype Vaccine Against *Streptococcus pneumoniae* infection", Science, vol. 223, (1984), pp. 1325–1326.

G.T. Nepom et al., "Induction of immunity to a human tumor marker by in vivo administration of anti–idiotypic antibodies in mice", Proc. Natl. Acad. Sci., vol. 81, (5/84), pp. 2864–2867.

A. Nisonoff et al., "Separation of Univalent Fragments from the Bivalent Rabbit Antibody Molecule by Reduction of Disulfide Bonds", Arch. Biochem. and Biphys., vol. 89, (1960), pp. 230–244.

M.J. Ostro et al., "Use of lisposomes as injectable–drug delivery systems", Am. J. of Hospital Pharmacy, vol. 46, (8/89), pp. 1576–1587.

R.R. Porter, "The Hydrolysis of Rabbit γ–Globulin and Antibodies with Crystalline Papain", The Biochemical Journal, vol. 73, No. 1, (9/59), pp. 119–127.

T.J. Powell et al., "Induction of Effective Immunity to Moloney Murine Sarcoma . . . Antibody as Immunogen", J. Immunology, vol. 142, No. 4, (2/89), pp. 1318–1324.

S. Raychaudhuri et al., "Tumor–specific Idiotype Vaccines", J. Immunology, vol. 139, No. 1, (7/87), pp. 271–278.

I.M. Roitt et al., Immunology 3rd Edition, pp. 7.8–7.14, (Mosby 1993).

G.L. Scherphof et al., "Uptake and Intracellular Processing of Targeted . . . In Vitro", Annals of the New York Academy of Sciences, vol. 446, (1985) pp. 368–384.

H. Schreier, "Liposome Aerosols", J. of Liposome Research, vol. 2, No. 2, (1992), pp. 145–184.

T. Stegmann et al., "Protein–mediated Membrane Fusion", Annu. Rev. Biophys. Biophys. Chem., vol. 18, (1989), pp. 187–211.

K.E. Stein et al., "Neonatal Administration of Idiotype or Antiidiotype Primes for Protection Against . . . in Mice", J. Exper. Med., vol. 160, (10/84), pp. 1001–1011.

P. Thomas et al., "The structure, metabolism and function of the carcinoembryonic antigen gene family", Biochimica et Biophysica Acta, 1032, (1990), pp. 177–189.

U.C. Traub et al., "Antiidiotype Antibodies in Cancer Patients Receiving Monoclonal Antibody to Carcinoembryonic Antigen", Cancer Research, vol. 48 (7/88), pp. 4002–4006.

T. Weber et al., "Evidence for H +–induced Insertion of Influenza Hemagglutinin HA2 N–terminal Segment into Viral Membrane", J. Biolog. Chem., vol. 269, No. 28, (7/94), pp. 18353–18358.

W.M. Yokoyama, "Production of Monoclonal Anbibodies", Current Protocols in Immunology, vol. 1, 1991, pp. 2.5.1–2.6.7.

S.P. Colowick et al., Methods in Enzymology, vol. 1., 1995.

* cited by examiner

VACCINE FOR B-CELL MALIGNANCIES

This application claims priority to provisional application Ser. No. 60/011,783, filed Feb. 16, 1996.

BACKGROUND OF THE INVENTION

1. Field of the Invention

The present invention relates to methods for inducing humoral and cellular immune responses against malignant B cells. In particular, this invention is directed to methods for producing an integrated immunologic response against tumor cells using antigens that are associated with a B-cell malignancy.

2. Background

One of the major goals of immunotherapy is to harness a patient's immune system against tumor cells or infectious organisms. With regard to cancer therapy, the objective is to direct the patient's immune system against tumor cells by targeting antigens that are associated with tumor cells, but not normal counterparts. These tumor associated antigens (TAAs) have been difficult to identify. Certain tumor cells express antigens that are normally not expressed, or expressed at very low levels, in adult life, although they are present during fetal development. One example of such oncofetal TAAs is $\alpha$-fetoprotein, which is expressed by liver cancer cells. Another oncofetal TAA is carcinoembryonic antigen (CEA), which is expressed in most adenocarcinomas of entodermally-derived digestive system epithelia, as well as in breast tumor cells and non-small-cell lung cancer cells. Thomas et al., *Biochim. Biophys. Acta* 1032: 177 (1990).

The administration of anti-idiotype antibodies (Ab2s) mimicking TAAs represents a promising approach to cancer immunotherapy. Goldenberg, Amer. *J. Med.* 94: 297 (1993). Ab2s are antibodies directed against the variable regions of conventional antibodies (Ab1). Certain Ab2s (termed "Ab2β", "anti-idiotype" or "internal-image" antibodies) can mimic the three-dimensional structure of the nominal antigen, and thus Ab2 and antigen can bind with the same regions of the Ab1-combining site. Jerne et al., *EMBO J.* 1: 243 (1982); Losman et al., *Int. J. Cancer* 46: 310 (1990); Losman et al., *Proc. Nat'l Acad. Sci. USA* 88: 3421 (1991); Losman et al., Int. J. Cancer 56: 580 (1994). Individuals immunized with Ab2B can develop anti-anti-antibodies (Ab3), some of which can bind the nominal antigen.

The antigen mimicry properties of anti-idiotype antibodies have led to the use of Ab2B as surrogate antigens (or idiotype vaccines), when the nominal antigen is not readily available or when the host is tolerant to the nominal antigen. In experimental systems, immunization with Ab2B mimicking certain TAA creates specific immunity to the TAA and protect against subsequent tumor growth. See, for example, Nepom et al., *Proc. Nat'l Acad. Sci. USA* 81: 2864 (1984); Raychaudhuri et al., *J. Immunol.* 139: 271 (1987). Similarly, anti-idiotype vaccines have been developed against infectious organisms, such as *Streptococcus pneumoniae* [McNamara et al., *Science* 226: 1325 (1984)], hepatitus B virus [Kennedy et al., *Science* 223: 930 (1984)], *Escherichia coli* K13 [Stein et al., *J. Exp. Med.* 160: 1001 (1984)], *Schistosomiasis mansoni* [Kresina et al., *J. Clin. Invest.* 83: 912 (1989)], and Moloney murine sarcoma virus [Powell et al., *J. Immunol.* 142: 1318 (1989)].

However, the usefulness of this approach is limited. Cancer patients receiving an anti-TAA of animal origin will usually produce antibodies to the Ab1 and these anti-immunoglobulin antibodies include Ab2. Herlyn et al., *J. Immunol. Methods* 85: 27 (1985); Traub et al., *Cancer Res.* 48: 4002 (1988). The anti-idiotype response also may include the generation of T cells (T2). Fagerberg et al., *Cancer Immunol. Immunother.* 37: 264 (1993). Moreover, Ab2 may subsequently induce a humoral and cellular anti-anti-idiotypic response, Ab3 and T3, respectively, which may recognize the same epitope as Ab1. Id. This is a problem because it can reduce the effectiveness of the immune response.

Thus, an opportunity exists to provide an approach to immunotherapy utilizing both humoral and cellular immune systems. The present methods to provoke an integrated response against tumor cells, particularly malignant B cells, is an initial result of this approach.

SUMMARY OF THE INVENTION

Accordingly, it is an object of the present invention to provide a vaccine and method of treatment by inducing humoral and cellular immune responses against malignant B cells, in particular lymphoma, chronic lymphocytic leukemia and multiple myeloma. The vaccine comprises a liposomal preparation that incorporates at least one B cell malignancy associated antigen, at least one cytokine, and at least one type of lipid molecule. This combination therefore provides a novel and more potent vaccine formulation for B cell malignancies. The B-cell malignancy-associated antigen is preferably derived from the patient to be treated and thus the vaccine will be directed against the patient's malignant B-cells.

Thus, in one embodiment, the invention provides a vaccine comprising a liposome preparation comprising (1) at least one B-cell malignancy-associated antigen; (2) IL-2, alone or in combination with at least one other cytokine; and (3) at least one type of lipid molecule.

In another embodiment, the B-cell malignancy-associated antigen comprises all or part of an antibody associated with or produced by a malignant B-cell. Such malignant B-cells include those associated with lymphoma, chronic lymphocytic leukemia and multiple myeloma. In a further embodiment, the vaccine of the invention additionally comprises a tumor-associated antigen that is not an antibody or antibody fragment. Examples of such additional TAAs include, e.g., MUC-1, Epstein Barr Virus (EBV) antigen or an antigen associated with Burkitt's lymphoma.

In an alternative embodiment, the vaccines of the invention additionally comprise normal B-cell antigens such as HLA antigens.

In another embodiment, the vaccine of the invention additionally comprises a another cytokine; examples of additional cytokines include M-CSF, GM-CSF and IFN-gamma.

The vaccines of the invention comprise at least one lipid molecule selected from the group consisting of phospholipid, cholesterol, and glycolipid and derivatives of these lipids. In a further embodiment, the vaccines of the invention also comprise a carrier protein, e.g., albumin.

In another embodiment, a method for inducing humoral and cellular immune responses against malignant B-cells in a mammal is provided, comprising administering to said mammal a vaccine comprising a liposome preparation comprising (1) at least one B-cell malignancy-associated antigen; (2) IL-2, alone or in combination with at least one other cytokine; and (3) at least one type of lipid molecule.

DETAILED DESCRIPTION

The vaccine is composed of three categories of molecules:
1. At least one B-cell malignancy associated antigen. Such an antigen is preferably an antibody, or a fragment of an antibody.
2. Cytokine, in the form of IL-2 alone or IL-2 plus one or more different cytokines such as IL-2, M-CSF, GM-CSF or IFN-gamma.
3. At least one type of lipid molecule, in the form of one or more phospholipids alone or in combination with one or more different lipids such as cholesterol.

The vaccine structure comprises a microscopic vesicle composed of lipid(s), cytokine(s) and at least one B-cell malignancy-associated antigen. The vaccine of the invention may also include an adjuvant or carrier protein, such as albumin.

1. Definitions

An antigen is a substance that, upon introduction into a vertebrate animal, stimulates the production of antibodies.

An idiotype is an antigenic determinant of the variable region of an antibody.

A B-cell malignancy associated antigen is a molecule produced by or associated with malignant B cells, but which is not normally expressed, or is expressed at very low levels, by a non-malignant B-cell. Examples of B-cell malignancy associated antigens include antibodies, antibody fragments produced by malignant B-cells, and other non-antibody antigens produced by or associated with malignant B-cells. Antibody fragments according to the invention normally comprise an idiotype.

A tumor cell associated antigen (TAA) is a molecule produced by or associated with malignant cells, but is not normally expressed, or expressed at very low levels, by a non-malignant cell.

A lipid is any of a group of biochemicals which are variably soluble in organic solvents, such as alcohol. Examples of lipids include phospholipids, fats, waxes, and sterols, such as cholesterol.

A vaccine is a material that is administered to a vertebrate host to immunize the host against the same material. Typically, a vaccine comprises material associated with a disease state, such as viral infection, bacterial infection, and various malignancies.

2. Production of Antigen a. B-cell malignancy-associated antibodies and antibody fragments An antigen according to the present invention can be an antibody molecule produced by the malignant B-cell or a fragment of such an antibody. In lymphoma, the antibodies associated with B cells typically contain a transmembrane domain. In chronic lymphocytic leukemia, such antibodies also have a transmembrane domain. In multiple myeloma, the malignant B-cells often secrete fragments of antibodies.

In one embodiment, these antibodies will be derived from the patient to be treated for B-cell malignancy. The antibodies can be extracted from a sample of tissue containing malignant B-cells which has been obtained from a patient with a B-cell malignancy. Typically such a tissue sample will be taken from the lymph nodes of the patient. In patients with multiple myeloma, antibodies can be extracted from the patient's serum and urine. It is known in the art that certain antibody light chain molecules are associated with multiple myeloma. One example of such a protein is a Bence-Jones protein. Using protein extraction and purification procedures well known to those of skill in the art, the B-cell antibodies can be isolated and purified. Such isolation and purification techniques include affinity chromatography, for example with protein-A sepharose, size exclusion chromatography and ion-exchange chromatography. See, for example, CURRENT PROTOCOLS IN IMMUNOLOGY, VOL 1, pages 2.7.1–2.7.12 (John Wiley & Sone 1991), METHODS IN MOLECULAR BIOLOGY, VOL. 10, pages 79–104 (The Humana Press, Inc. 1992). It is also known in the art that three major idiotypes are associated with chronic lymphocytic leukemia.

In another embodiment, the patient tissue sample containing malignant B cells will be used to create monoclonal antibodies in vitro. Typically, malignant tissue, containing malignant B-cells is fused with a mouse cell line to produce a hybridoma cell line that will produce a malignant B-cell-associated antibody. Techniques for making monoclonal antibodies are well known to those of skill in the art. See, for example, Kohler and Millstein, *Nature* 256: 495 (1975) and CURRENT PROTOCOLS IN IMMUNOLOGY, VOL 1, pages 2.5.1–2.6.7 (John Wiley & Sone 1991)

In one embodiment, the antigen will comprise a fragment of an antibody produced by malignant B-cells. Normally, such a fragment will comprise an idiotype associated with the malignant B-cell. An antibody fragment according to the invention includes (A) a "half antibody" molecule, i.e., a single heavy:light chain pair, and (B) an enzymatically cleaved antibody fragment, such as the univalent fragments Fab and Fab', the divalent fragment $F(ab')_2$, and a single or double chain Fv fragment. An Fv fragment of an antibody is made up of the variable region of the heavy chain (Vh) of an antibody and the variable region of the light chain of an antibody (Vl).

In accordance with the present invention, fragments within the invention can be obtained from an antibody by methods that include digestion with proteases such as pepsin or papain and/or cleavage of disulfide bonds by chemical reduction. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1–2.8.10 and 2.10.–2.10.4.

Alternatively, antibody fragments encompassed by the present invention can be synthesized using an automated peptide synthesizer such as those supplied commercially by Applied Biosystems, Multiple Peptide Systems and others, or they may be produced manually, using techniques well known in the art. See Geysen et al., *J. Immunol. Methods* 102: 259 (1978). Direct determination of the amino acid sequences of the variable regions of the heavy and light chains of the antibodies according to the invention can be carried out using conventional techniques.

Proteolytic cleavage of an antibody can produce double chain Fv fragments in which the Vh and Vl regions remain non-covalently associated and retain antigen binding capacity. Double chain Fv fragments also can be produced by recombinant expression methods well known in the art. See Skerra et al., *Science* 240: 1038 (1988), and King et al., *Biochemical J.* 290: 723 (1991). Briefly, the amino acid sequence of the variable regions of the heavy and light chains of antibodies according to the invention can be obtained by direct amino acid sequencing using methods well known to those in the art. From this amino acid sequence, synthetic genes can be designed which code for these variable regions and they can both be inserted into an expression vector. Two polypeptides can be expressed simultaneously from a mammalian or bacterial host, resulting in formation of an active Fv fragment.

An antigen of the present invention also can be a "single chain antibody," a phrase used in this description to denote a linear polypeptide that binds antigen with specificity and that comprises variable or hypervariable regions from the heavy and light chain chains of an antibody. Other single chain antibodies according to the invention can be produced by conventional methodology. The Vh and Vl regions of the Fv fragment can be covalently joined and stabilized by the insertion of a disulfide bond. See Glockshuber, et al., *Biochemistry* 1362 (1990). Alternatively, the Vh and Vl regions can be joined by the insertion of a peptide linker. A gene encoding the Vh, Vl and peptide linker sequences can be constructed and expressed using a recombinant expression vector. See Colcher, et al., *J. Nat'l Cancer Inst.* 82: 1191 (1990). Amino acid sequences comprising hypervariable regions from the Vh and Vl antibody chains can also be constructed using disulfide bonds or peptide linkers, as described herein.

Another form of an antibody fragment is a peptide constituting a single complementarity-determining region (CDR). CDR peptides, such as CDR3, ("minimal recognition units") can be obtained by constructing and expressing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991).

b. Non-malignancy associated B-cell antigens

The vaccines of the invention can also comprise B-cell antigens which are not specifically associated with malignant B-cells ("non-malignancy associated B-cell antigens"). Examples of these antigens are known in the art and include CD19, CD20, CD21, CD22, CD23, CD25, CD5, and FMC7. Foon, K. *Stem Cells* 13(1):1–21 (1995). Also included in this group are class 1 and class 2 HLA antigens (histocompatibility molecules). Class 1 HLA antigens are also found on almost all other mammalian cells.

c. Other tumor-associated antigens (TAAs)

The vaccines of the invention can additionally comprise other TAAs. Examples of such tumor-associated antigen are MUC-1, EBV antigen and antigens associated with Burkitt's lymphoma.

3. Preparation of Liposome

Liposomes are microscopic vesicles that consist of one or more lipid bilayers surrounding aqueous compartments. See, generally, Bakker-Woudenberg et al., *Eur. J. Clin. Microbiol. Infect. Dis.* 12 (Suppl. 1): S61 (1993), and Kim, *Drugs* 46: 618 (1993). Liposomes are similar in composition to cellular membranes and as a result, liposomes generally can be administered safely and are biodegradable. Depending on the method of preparation, liposomes may be unilamellar or multilamellar, and liposomes can vary in size with diameters ranging from 0.02 $\mu$m to greater than 10 $\mu$m. A variety of agents can be encapsulated in liposomes: hydrophobic agents partition in the bilayers and hydrophilic agents partition within the inner aqueous space(s). See, for example, Machy et al., LIPOSOMES IN CELL BIOLOGY AND PHARMACOLOGY (John Libbey 1987), and Ostro et al., *American J. Hosp. Pharm.* 46: 1576 (1989).

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents. Scherphof et al., *Ann. N.Y. Acad. Sci.* 446: 368 (1985).

Among liposome vectors, cationic liposomes are the most studied, due to their effectiveness in mediating mammalian cell transfection in vitro. They are often used for delivery of nucleic acids, but can be used for delivery of other therapeutics, be they drugs or hormones.

Cationic lipids are not found in nature and can be cytotoxic, as these complexes appear incompatible with the physiological environment in vivo which is rich in anionic molecules. Liposomes are preferentially phagocytosed into the reticuloendothelial system. However, the reticuloendothelial system can be circumvented by several methods including saturation with large doses of liposome particles, or selective macrophage inactivation by pharmacological means. Claassen et al., *Biochim. Biophys. Acta* 802: 428 (1984). In addition, incorporation of glycolipid- or polyethelene glycol-derivatised phospholipids into liposome membranes has been shown to result in a significantly reduced uptake by the reticuloendothelial system. Allen et al., *Biochim. Biophys. Acta* 1068: 133 (1991); Allen et al., *Biochim. Biohys. Acta* 1150: 9 (1993).

Anionic liposomal vectors have also been examined. These include pH sensitive liposomes which disrupt or fuse with the endosomal membrane following endocytosis and endosome acidification.

Liposome complexes are sometimes targeted to the cell type or tissue of interest by the addition to the liposome preparation of a ligand, usually a polypeptide, for which a corresponding cellular receptor has been identified. An example of a cell receptor that can be targeted is the folate receptor which has recently been identified as a prominent tumor marker, especially in ovarian carcinomas. KB cells are known to vastly overexpress the folate receptor. Campbell et al., *Cancer Res.* 51: 6125–6132 (1991). Yet other targeting ligands have been examined for liposome targeting including transferrin, protein A, ApoE, P-glycoprotein, $\alpha_2$-macroglobin, insulin, asiolofetuin, asialoorosomucoid, monoclonal antibodies with a variety of tissue specificity, biotin, galactose or lactose containing haptens (monovalent and tri-antennary), mannose, dinitrophenol, and vitamin B12. The ligands are covalently conjugated to a lipid anchor in either pre-formed liposomes or are incorporated during liposome preparation. Lee and Low *J. Biol. Chem.* 269: 3198–3204 (1994) and Lee and Low *Biochim. Biophys. Acta* 1233: 134–144 (1995).

Synthetic peptides are sometimes incorporated into DNA/liposome complexes to enhance their activity, or to target them to the nucleus. For example, in order to gain access to the cytoplasm, the molecule to be delivered must overcome the plasma membrane barrier. In nature, viral fusion peptides facilitate the delivery into the cytoplasm by promoting viral membrane fusion with the plasma membrane. For recent reviews on this subject see Stegmann et al., Ann. Rev. Biophys. Chem. 18: 187–221 (1989). For the influenza virus, the hemagglutinin (trimer) HA peptide N-terminal segment (a hydrophobic helical sequence) is exposed due to a conformational change induced by acidic pH in the endosomes (pH 5–6), inserts into the target membrane, and mediates the fusion between the virus and the target endosomal membrane. Weber et al., *J. Biol. Chem.* 269: 18353–58 (1994). Recently, several amphipathic helix-forming oligopeptides have been designed to imitate the behavior of the viral fusion peptide. See, for example, Haensler and Szoka, *Bioconj. Chem.* 4: 372–79 (1993).

Cationic liposome preparations can be made by conventional methodologies. See, for example, Felgner et al., *Proc. Nat'l Acad. Sci USA* 84:7413 (1987); Schreier, *J. of Liposome Res.* 2:145 (1992); Chang et al. (1988), supra. Commercial preparations, such as Lipofectin® (Life Technologies, Inc., Gaithersburg, Md. USA), also are available. For some recent reviews on methods employed see Wassef et al., *Immunomethods* 4: 217–222 (1994) and Weiner, A. L., *Immunomethods* 4: 217–222 (1994).

It is possible to control the therapeutic availability of the encapsulated agent by varying liposome size, the number of bilayers, lipid composition, as well as the charge and surface characteristics of the liposomes. The liposomal preparation could contain one or more adjuvants. Furthermore, a carrier protein such as serum albumin can be added.

4. Delivery of the liposome preparation

In general, the dosage of administered liposome preparation will vary depending upon such factors as the patient's age, weight, height, sex, general medical condition and previous medical history. Dose ranges for particular formulations can be determined by using a suitable animal model.

Liposomes may be administered to a subject intravenously., intraperitoneally, intrathecally, intramuscularly or subcutaneously. See, for example, Kim, supra, Bakker-Woudenberg et al. (1993), supra, Allen et al. (1993), supra, and Fielding et al., *Clin. Pharmacokinetics* 21: 155 (1991).

For purposes of therapy, antibodies or fragments are administered to a mammal in a therapeutically effective amount. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes a humoral and/or cellular immune response in the recipient mammal.

5. Cytokines

The vaccines of the present invention comprise cytokines. Examples of cytokines include the interferons (INFS) such as INF-gamma, interleukins (ILs), M-CSF, GM-CSF, and tumor necrosis factor. INF-$\gamma$ induces macrophages, as well as cell-surface class II histocompatibility antigens on lymphoid cells and monocytes. See, for example, Klegerman et al., "Lymphokines and Monokines," in BIOTECHNOLOGY AND PHARMACY, Pezzuto et al. (eds.), pages 53–70 (Chapman & Hall 1993), and Roitt et al., IMMUNOLOGY, 3rd Edition, pages 7.8–7.14 (Mosby 1993). IL-2 is a T cell growth factor and a stimulator of natural killer cells and tumor-reactive T cells. Id. Thus, INF-$\gamma$ and IL-2 are preferred cytokines for the augmentation of the immune response.

6. Examples

ONCOVAX MATERIALS:

Mouse antigen 38cId

DMPC: Survival Tech Lot RD 1426

MSA 25%): Biocell Laboratories, CAlot#4002160

IL-2: Survival Tech. Lot #RD 1534 @9.38 mg/ml)

OTx Buffer

PEG

To 50–200 mg of DMPC or DMPC/DMPG ata ratio of 4/1, the following is added such that the final volume is between 0.4–1.0 ml:

0.3–10 mg of antigen, i.e. 38cId 0.0–7×10$^6$ IU of IL-2

0.0–12 mg mouse serum albumin

EXAMPLE 1

(freeze-thaw procedure for preparation of the vaccine):

Mix aqueous components. Add to the powdered lipid in a 5 mL vial glass vial. Warm for 10 minutes in a 35–39° C. water bath. Vortex for 30 seconds. Bath sonicate at 25–45° C. for 15 minutes. Freeze the vials in a dry ice/ethanol bath at −80° C. for 15 minutes. Thaw in a 35–39° C. water bath for 10 minutes. Repeat the vortexing, sonication, freezing and thawing steps a total of three (3) times. Add aqueous buffer to dilute as necessary. The sample may be washed by centrifugation. Centrifuge at 12,000 rpm for 20 minutes. Remove supernatant and wash two more times.

EXAMPLE 2

(sonication-fusion procedure for preparation of the vaccine):

Hydrate the lipid in aqueous buffer at a concentration of 100–300 mg/mL. Sonicate in a bath sonicator at 30–45° C. until clear. Sterile filter through a 0.2 micron filter. Add antigen, IL-2 and serum albumin. Cool sample 4–15° C. This may be temperature cycled any number of times from −80° C. to 15° C. as the low temperature to 23° C. to 50° C. as the high temperature. The sample may be diluted as necessary, and washed by centrifugation as in Example 1.

EXAMPLE 3

(PEG-fusion procedure):

Hydrate the lipid in aqueous buffer at a concentration of 100–300 mg/mL. Sonicate in a bath sonicator at 30–45° C. until clear. Sterile filter through a 0.2 micron filter. Add antigen, IL-2 and mouse serum albumin. Mix with an equal volume of PEG solution of MW 1,000 on up to 20,000. The PEG solution should be between 6% to 60% w/v. Following an incubation at 4° C. to 25° C. for one to 24 hours, washing by centrifugation will remove the PEG and unincorporated active ingredients.

EXAMPLE 4

(extrusion procedure):

The sample from Examples 1–3 may be size-reduced by extrusion through a 1.0, 0.4 and 0.2 micron polycarbonate filter. The final size should be between 100–200 nm.

The vaccine products under this disclosure are called OncoVAX. Each OncoVAX preparation as well as the (KLH-Id) control was analyzed by determining the amount of antigen (Id), IL-2 and lipid as well as the size of OncoVAX particles.

Final concentrations (ranges) of the structural components of OncoVAX were as follows:

TABLE 1

| Structural Component | Example | | | | Control |
|---|---|---|---|---|---|
| | #1 | #2 | #3 | #4 | (KLH-Id) |
| Lipid (mg/mL) | 20–60 | 3–30 | 20–60 | 20–60 | none |
| Antigen Id mcg/mL | 1–200 | 1–2,000 | | 1–200 | 500–1,000 |
| IL-2 (IU/mL) × $10^4$ | 1–200 | 1–200 | | 1–200 | none |
| Mean Size (micron) | 2–4 | 1–2 | | 0.1–0.3 | Soluble (no particle) |

The following are examples of the characterization of oncovax and the mouse studies exhibiting the antitumor immunity, effective liposomal dose with respect to antigen and IL-2 content, humoral and cellular responses elicited by liposomal vaccines, and the effect on in vivo T cell depletion.

The antigen concentration was determined by a sandwich ELISA method where to unknown antigen bound to rabbit anti mouse IgM a biotinylated rabbit anti mouse IgM was added. To this streptavidin-Europium was added and the Europium fluorescence was measured.

EXAMPLE 5

(Characterization of a typical Oncovax preparation.)

Figure 1A:
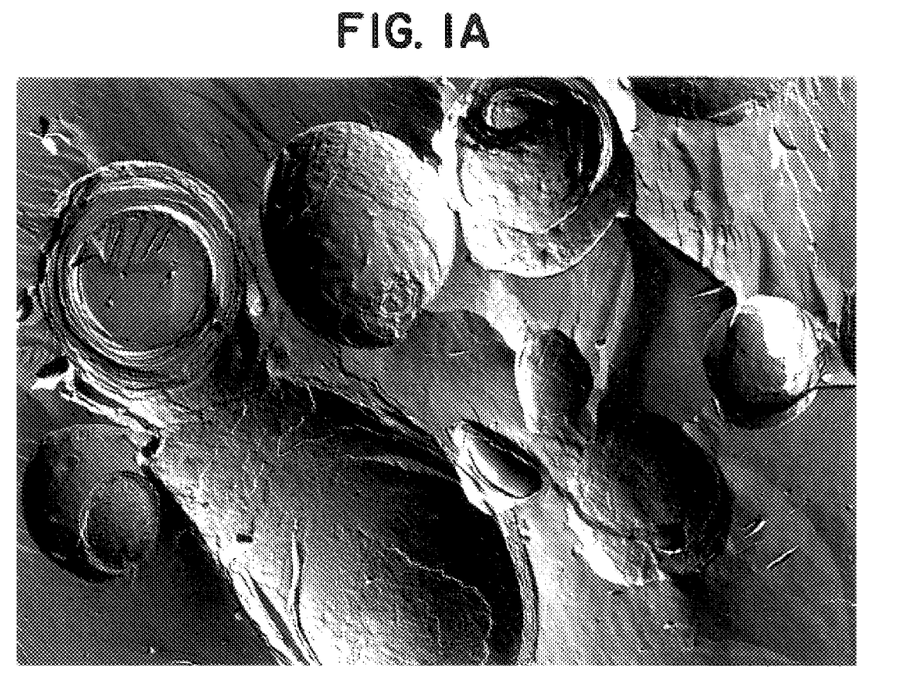
FIGS. 1A, 1B and 1C show features of liposomes prepared according to the invention.
Figure 1B:
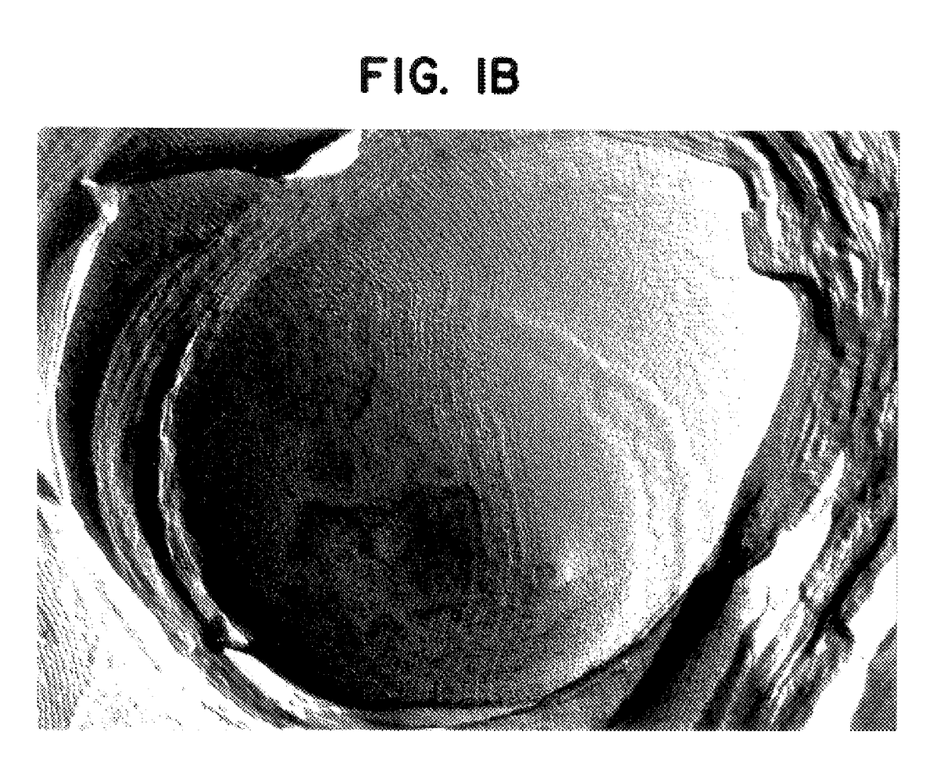
Figure 1C:
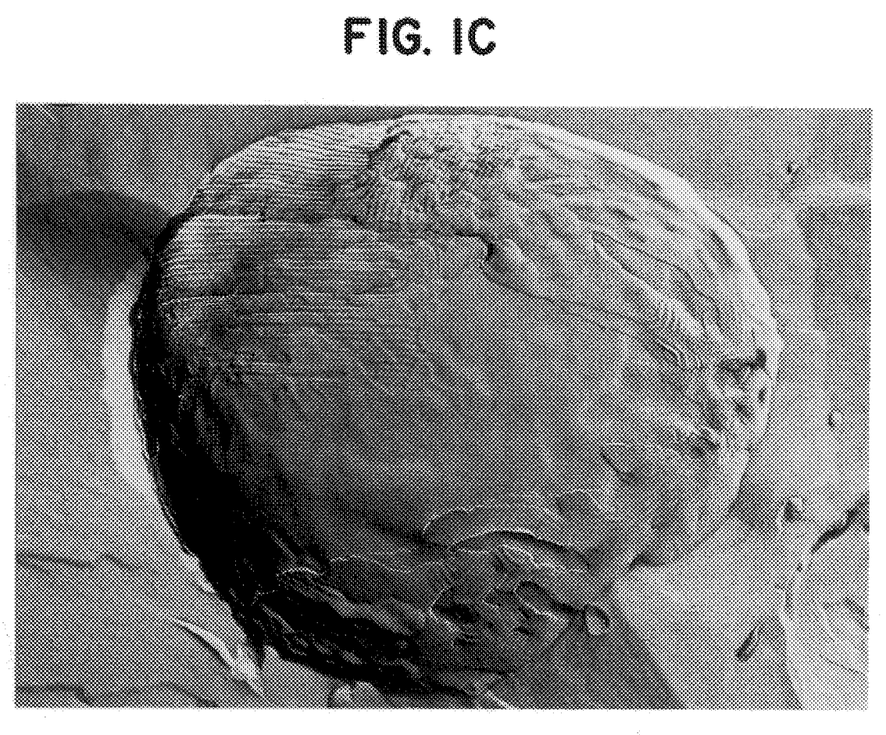
Figure 2:
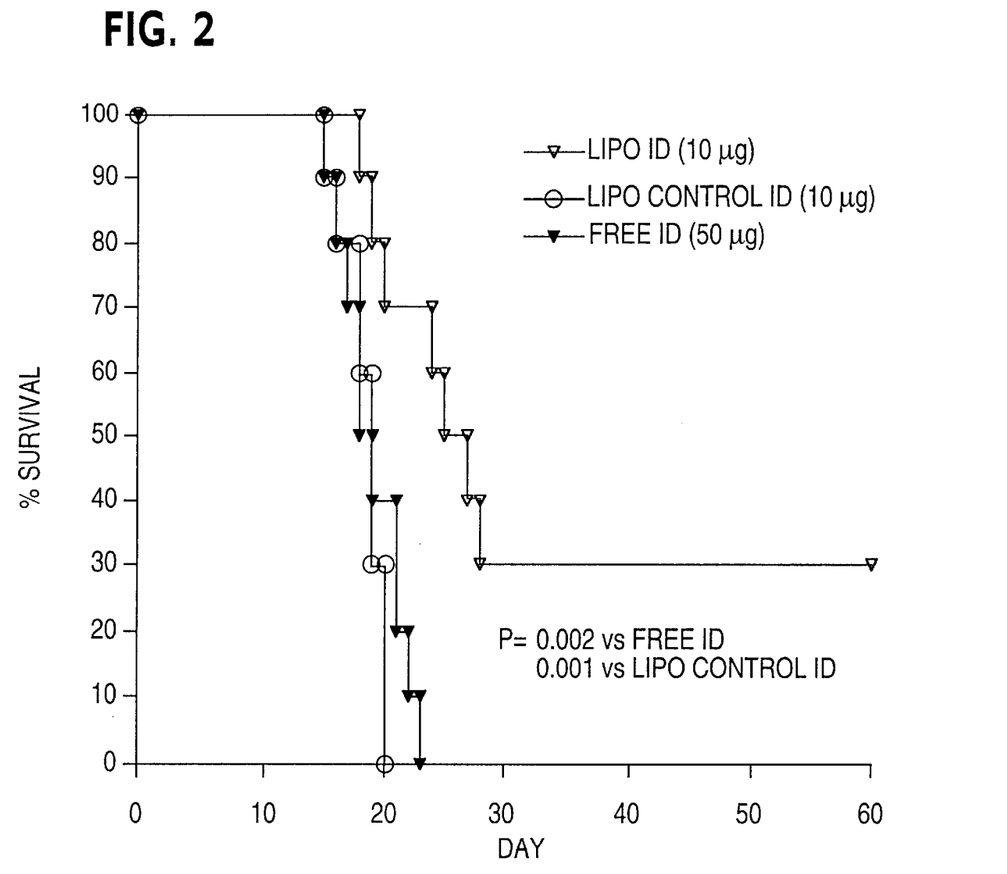
FIG. 2 shows survival rates of immunized and control mice according to Example 2.
Figure 3:
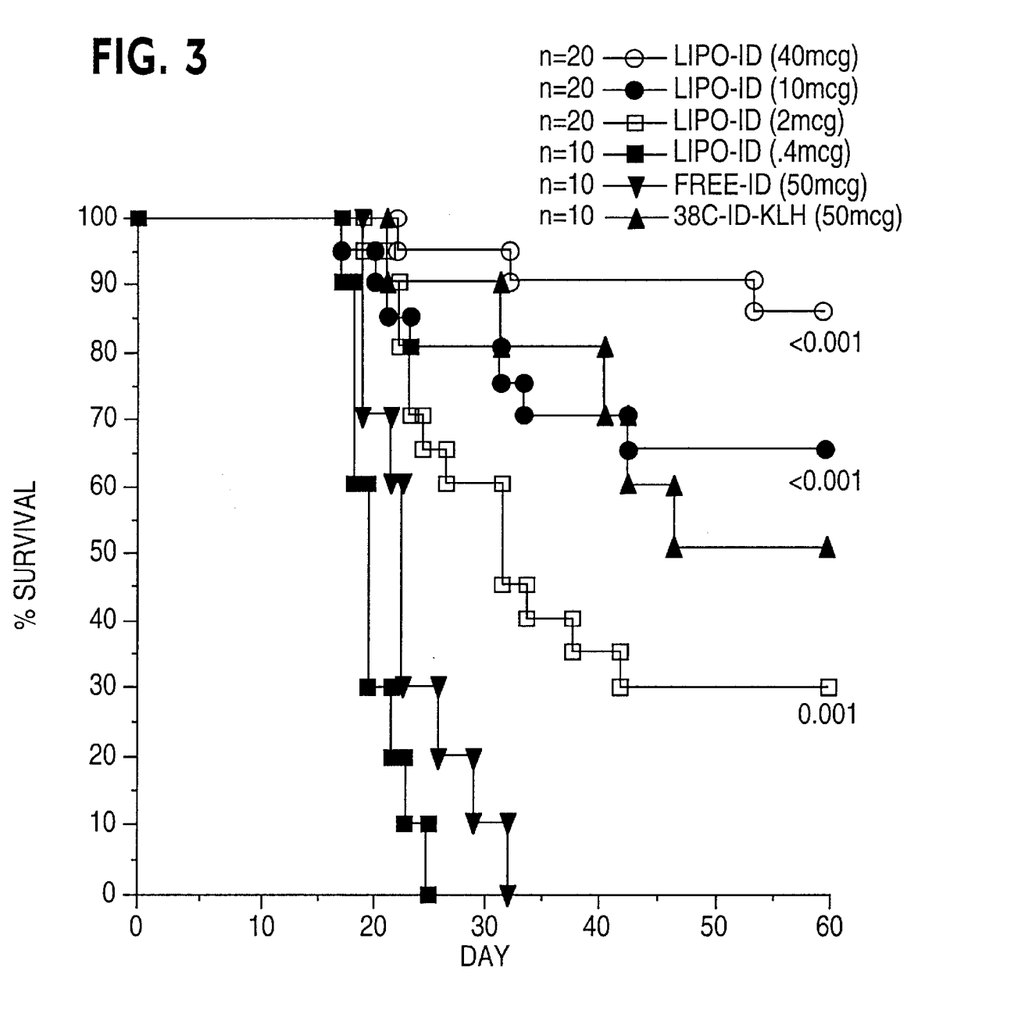
FIG. 3 shows survival rates of immunized and control mice according to Example 3.
Figure 4:
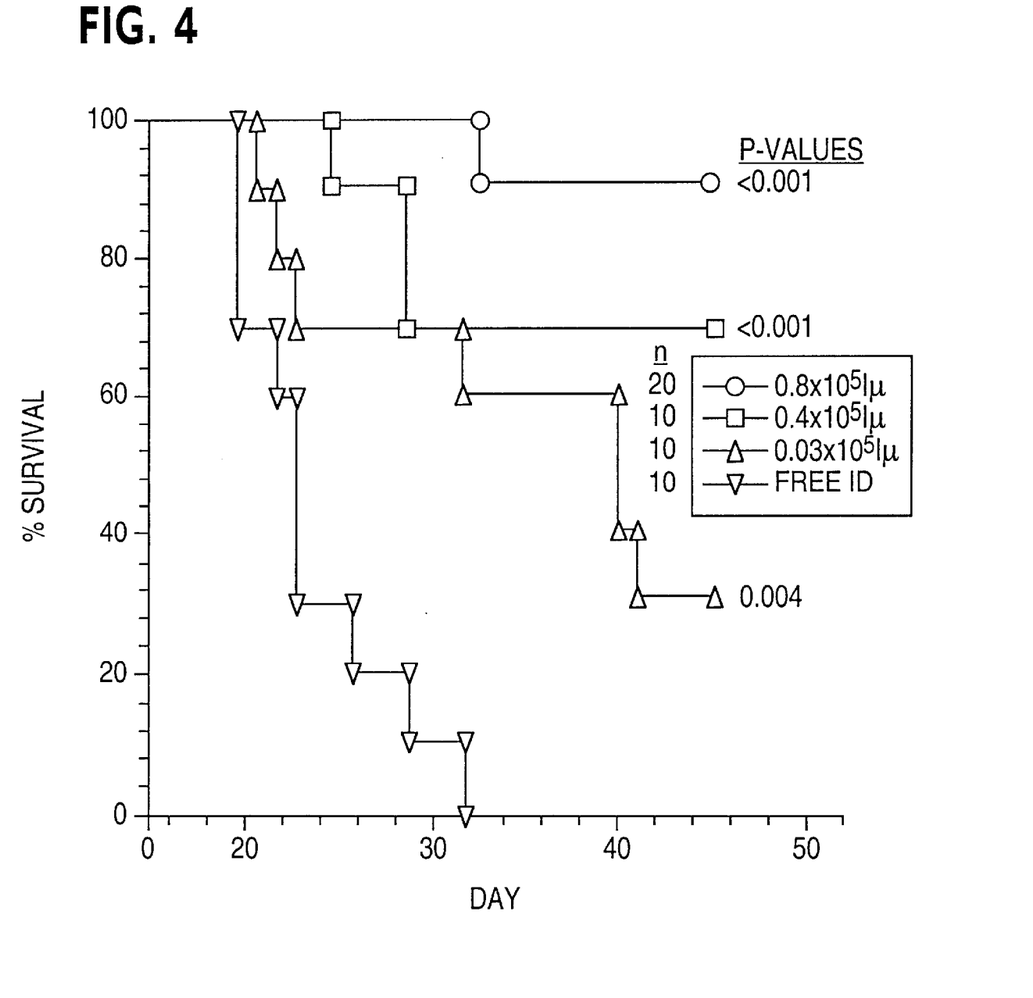
FIG. 4 shows survival rates of immunized and control mice according to Example 5.
Figure 5:
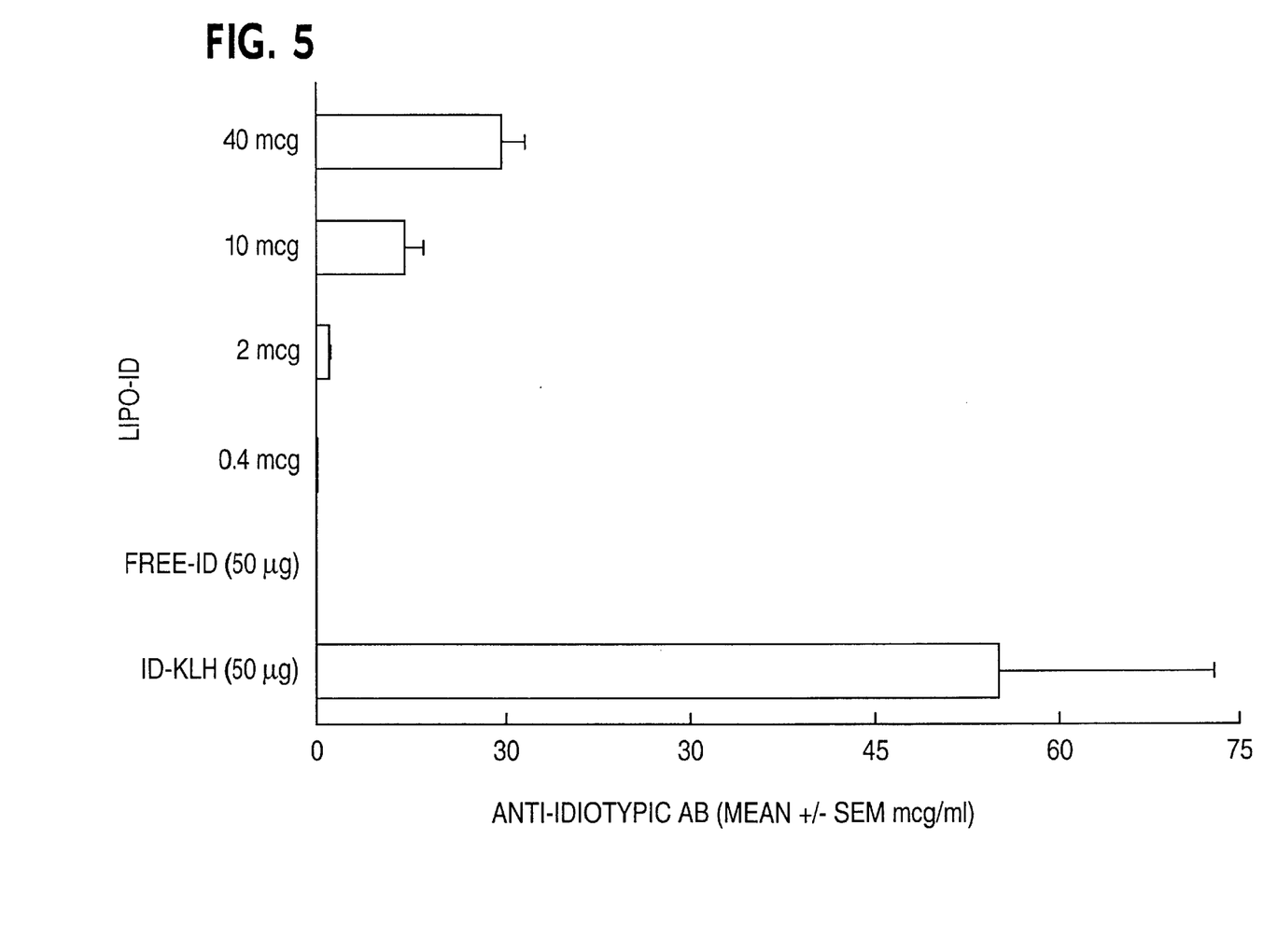
FIG. 5 shows anti-idiotype titers as a function of IL-2, according to Example 6.
Figure 6:
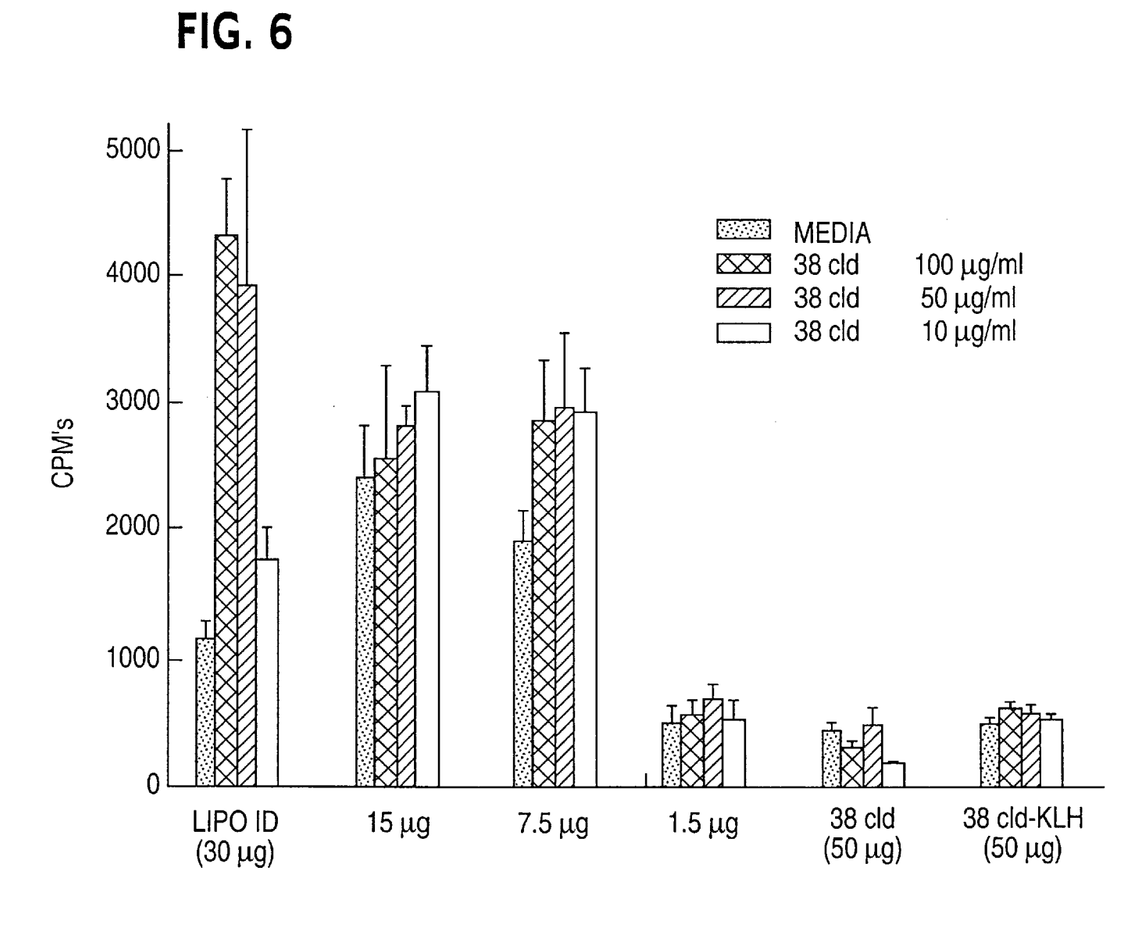
FIG. 6 shows T-cell proliferation as a function of vaccine dose, according to Example 7.
Figure 7:
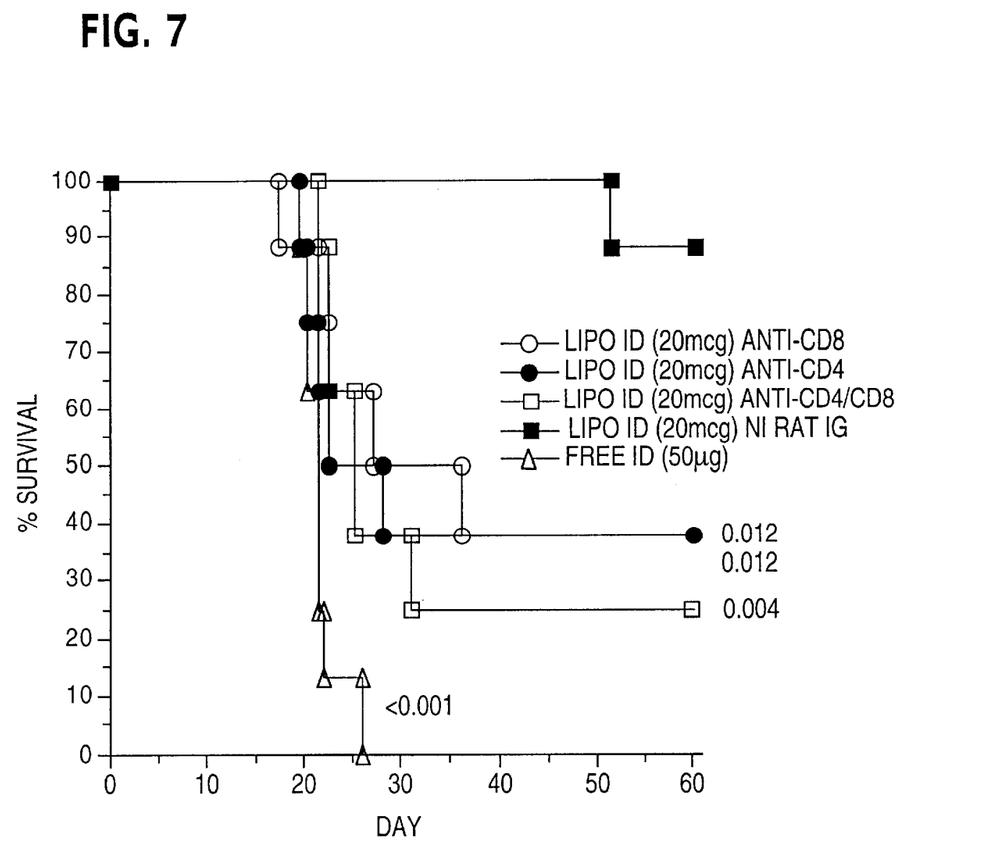
FIG. 7 shows survival rates for immunized and control mice according to Example 8.

Samples were rapidly frozen from room temperature between copper planchets without cryoprotectant in liquid propane and replicated in a Balzers freeze-fracture unit, and viewed on a Philips 300 electron microscope. FIG. 1A reveals the multilamellar liposomes formed. The mean size is roughly 3.0 microns, as determined by single-particle optical sensing (SPOS). FIG. 1B reveals a surface texture with numerous bulges and abrupt changes in the ripple patterns. A smooth ripple pattern is characteristic of DMPC liposomes at room temperature, as seen in FIG. 1C, the control DMPC liposomes with mouse serum albumin. Bar= 0.4 microns.

EXAMPLE 6

(Immunity test)

To determine whether liposomal formulation of Id could produce the acquisition of protective antitumor immunity, ten syngenic C3H/HEN mice per group were immunized i.p. with liposomal Id or control Id preparations, or with 50 ug 38C13-derived Id in PBS in a volume of 0.2 ml. Two weeks later the mice were challenged with a lethal dose of $2 \times 10^3$ 38C13 cells. Statistical comparisons of survival were made on the basis of nonparametric mantel-log rank p values. Mice surviving greater than 90 days after tumor challenge were euthanized and reported as long term survivors. Immunization with liposomal Id demonstrated significantly prolonged survival as well as protection (30%).

EXAMPLE 7

(Optimization of liposomal vaccine potency and comparison of potency with XLH conjugated Id vaccine.)

Serial dilutions of input Id antigen were made to prepare for liposomal vaccines which were otherwise identical. The actual amounts of incorporated Id were determined for each vaccine after preparation as outlined previously. Id-KLH was prepared by gluteraldehyde conjugation at a 1:1 ratio of Id and KLH and the dose of Id administered per animal as indicated in parenthesis. A clear dose dependent effect on the induction of protective antitumor immunity was observed, with mice receiving liposomal vaccine formulations delivering 40, 10, and 2 ug Id per mouse demonstrating significantly superior survival compared with controls immunized with free Id. Mice immunized with liposomal vaccines delivering 0.4 ug Id per mouse were not protected from subsequent tumor challenge.

EXAMPLE 8

The potency of a representative liposme vaccine containing low amount of Id, compared with serial dilutions of ID-KLH in PBS was examined. Previous studies have determined 50 ug Id in the conjugate formulation to be the optimal dose. Ten mice per group immunized with Id-KLH containing 50, 10, or 2 ug Id per mouse demonstrated 40, 30, and 0 percent protection, respectively, compared with nine mice immunized with a liposomal vaccine containing 2 ug ID, which demonstrated 33% protection from subsequent lethal dose tumor challenge (log rank p=0.007 compared with Id-KLH 2 ug Id dose).

EXAMPLE 9

The requirement for IL-2 as a component of the liposomal Id vaccine formulation was investigated by preparing several formulations with serial dilutions of input IL-2, holding the other components constant. Mice immunized with the resulting liposomal formulations, all containing a dose of 40 ug Id, were used to immunize mice. Two weeks later all mice were challenged with $2 \times 10^3$ $^{38}$C13 cells from a single preparation of tumor and followed for survival. The log rank p values refer to comparisons against three Id groups. The survival patterns of these mice following lethal dose tumor challenge shows a clear IL-2 dose-dependence on the induction of protective antitumor immunity. Other experiments demonstrating the failure of liposomal Id vaccines not containing IL-2 to induce any significant antitumor immunity support the conclusion that IL-2 is a critical component of the vaccine formulation, although liposomal vaccines containing 1/10 the amount of input IL-2 were capable on inducing significant protective antitumor immunity (log rank p 0.004 vs. free Id).

EXAMPLE 10

In an effort to investigate the cellular mechanism by which liposomal Id vaccines promote the acquisition of protective antitumor immunity, we first determined serum anti-idiotypic antibody levels elicited by the various liposomal vaccine formulations containing different doses of Id in the mice. Individual serum samples were assayed for binding to Id-coated microtitered plates in a direct ELISA. The specificity of the antibody response for idiotype was demonstrated by the lack of binding to control IgM proteins. Serum samples were collected from five individual mice per group two weeks after immunization, just prior to tumor challenge, and the mean anti-idiotypic antibody levels are shown. A clear dose dependent effect of the liposome-entrapped Id was apparent, with mean anti-idiotypic antibody levels of 15, 7, 1, and 0.1 ug/ml detectable by ELISA. This demonstration of humoral response specific for idiotype in the three liposomal vaccine groups containing 2, 10, and 40 ug Id stood out in stark contrast to free Id, which failed to induce any detectable anti-idiotlypic antibody even in a single immunized mouse. However, the mean levels of anti-idiotypic antibody elicited by liposomal Id vaccines was considerably less than that elicited by ID-KLH (55 ug/ml serum).

EXAMPLE 11

Because the magnitude of the anti-idiotyic antibody response did not correlate entirely with the relative levels of protection induced by liposomal Id vaccines and the Id-KLH, we also examined evidence for idiotype-specific T cell activation. Splenocytes obtained from 2–3 mice per group which had been immunized i.p. as indicated two weeks earlier were pooled and enriched by T cells passed over nylon wool and placed in 96 well bottomed microliter plates with Id at various concentrations (200 ul, $2\times10^5$ cells/well). Irradiated (2000 rads) spleen cells from normal syngenic mice were also added to splenocyte cultures ($2\times10^5$) as a source of antigen presenting cells. Cultures were maintained at 37° C., 5% $CO_2$ for 5–7 days, and 18–24 hours before harvesting 1 uCi [$^3$H-thymidine] (2Ci/mmol, New England Nuclear Research Products, Boston, Mass.) in 50 ul medium to each well. Incorporated radioactivity was measured in an LKB 1205 beta plate liquid scintillation counter. All determinations were performed in quadruplicate and the data are presented as the mean CPM plus standard error of the mean. Splenic T cells obtained from mice given a single immunization with a liposomal Id vaccine, empty liposomes, free Id, or Id-KLH two weeks earlier were assayed in vitro for proliferative responses to various doses of Id. The representative experiment demonstrates a significant T cell proliferative response to Id but not among groups primed with empty liposomes or free Id. These results are also particularly revealing, because such evidence of T cell activation has never been observed after immunization with Id-KLH and was not observed with an Id-cytokine fusion protein.

EXAMPLE 12

To definitively establish the role of idiotype-specific T cells in the effector phase of induced protective antitumor immunity, we tested the effect of T cell subset depletion in vivo in immunized mice. Mice were immunized with a single liposomal Id vaccine preparation two weeks after immunization, eight mice per group were randomly assigned to receive treatment with depleting mAb specific for either CD4+ ((GK1.5, ammonium sulfate purified assightese from the BRMP pre-clinical repository, Frederick, Md.), CD8+ T cells (53.6–72, ammonium sulfate purified assightese from the BRMP pre-clinical repository, Frederick, Md.), a combination of the two antibodies, or with normal rat IgG (Sigma, St. Louis, Mo.) every other day for three doses, just prior to challenge with a single preparation of tumor. Three weeks after immunization, all mice were challenged i.p. with $2\times10^3$ 38c13 cells from a single preparation of tumor and were followed for survival. Depletion of lymphocyte subsets was assessed one and two weeks after final treatment by flow cytometric analysis of spleen cells from normal mice treated with monoclonal antibodies in parallel. For both timepoints of analysis, greater than 95% depletion of the appropriate subset was achieved with normal levels of the other subsets. As shown, depletion of either CD4+ or CD8+T cells among immunized mice was associated with marked reduction of protective antitumor immunity (log rank p=0.012 for either group vs. liposomal Id immunized, normal rat Ig-treated mice). Although mAb treated groups were not significantly different compared with control mice immunized with free Id (log rank p=0.09 and 0.16, respectively, vs. free Id). Combined treatment with anti-CD4 and anti-CD8 mAbs did not result in further abrogation of protection (log rank p=0.10 vs. free Id). Thus, it appears clear that there is an absolute requirement for both CD4+and CD8+ effector T cells in liposomal Id vaccine induced protective antitumor immunity.

EXAMPLE 13

As an initial step towards testing liposomal Id immunization against previously established tumors we performed experiments in which tumor challenge was performed first, followed by vaccination later the same day. For these studies we modified an existing protocol vaccination against subcutaneous 38C13 tumors which required a non-curative dose of cyclophosphamide (CTX) chemotherapy on day ten to retard the growth of this virulent tumor. Mice were injected with $10^4$ tumor cells subcutaneously in the flank and then randomly assigned to immunization with liposomal Id, liposomal control Id vaccines, or PBS i.p. later the same day. The subcutaneous route of tumor inoculation was used because of the availability of tumor size monitoring as a surrogate endpoint for survival, and by day ten all mice developed macroscopic, palpable tumor masses of approximately 1 cm diameter. CTX administration (75 mg/kg i.p.) was associated with complete disappearance of tumors which was uniformly transient in all control mice but durable in a modest but significant proportion of mice immunized with liposomal Id vaccines (log rank p=0.01 for pooled liposomal Id vs. control groups).

TABLE 2

Therapeutic effect of Lip Id vaccines against a large s.c. tumor inoculum.

| Exp. | Immunogen | No. Survivors/Total no. mice |
|---|---|---|
| 1 | Lipo Id (10 µg) | 2/10 |
|  | Lipo control Id (10 µg) | 0/5 |
|  | PBS | 0/5 |
| 2 | Lipo Id (20 µg) | 3/10 |
|  | PBS | 0/10 |

C3H mice were injected with $10^4$ 38C13 tumor cells s.c. and then immunized i.p. as indicated later the same day (day 0). All groups received CTX 75 mg/kg i.p. on day 10. Mice surviving >60 days without tumor relapse were apparently cured.

Although the foregoing refers to particular embodiments, it will be understood that the present invention is not so limited. It will occur to those of ordinary skill in the art that various modifications may be made to the disclosed embodiments and that such modifications are intended to be within the scope of the present invention.

What is claimed is:
1. A therapeutic liposomal composition comprising
   a) at least one B-cell malignancy-associated antigen;
   b) IL-2, alone or in combination with at least one other cytoldne; and c) at least one lipid, wherein said IL-2 is present in a amount sufficient to induce humoral and cellular immune responses against malignant B-cells in a mammal and wherein said antigen is unconjugated and comprises an immunoglobulin or an immunoglobulin fragment contains anidotype said immunoglobulin or said fragment being associated with a malignant B-cell.

2. A composition according to claim 1, wherein said malignant B cell is associated with lymphoma.

3. A composition according to claim 1, wherein said malignant B cell is associated with chronic lymphocytic leukemia.

4. A composition according to claim 1, wherein said malignant B cell is associated with multiple myeloma.

5. A composition according to claim 1, additionally comprising tumor associated antigen that is not an immunoglobulin or immunoglobulin fragment.

6. A composition according to claim 1, further comprising a B-cell antigen produced by or associated with non-malignant B-cells.

7. A composition according to claim 6, wherein said B-cell antigen is a class 1 or class 2 HLA antigen.

8. A composition according to claim 1, wherein said at least one other cytokine is selected from the group consisting of M-CSF, GM-CSF, and IFN-gamma.

9. A composition according to claim 1, wherein said lipid molecule is selected from the group consisting of phospholipid, glycolipid, cholesterol, and derivatives of said lipids.

10. A composition according to claim 1, further comprising a carrier protein.

11. A composition according to claim 10, wherein said carrier protein is albumin.

12. A composition according to claim 1, further comprising a pharmaceutically acceptable vaccine vehicle.

13. A method for inducing humoral and cellular immune responses against malignant B-cells in a mammal, comprising administering to said mammal a composition according to claim 12.

14. A composition according to claim 1, wherein the IL-2 in said liposomal composition is present in a concentration of at least $3 \times 10^3$ IU/ml.

15. A composition according to claim 14, wherein the IL-2 is present in a concentration of at least $1 \times 10^4$ IU/ml of vaccine.

16. A composition according to claim 14, wherein said B-cell malignancy-associated antigen is present from about 1 to 200 µg/ml.

17. A method of treating a mammal suffering from a B-cell malignancy, comprising administering to said mammal an effective amount of a therapeutic composition according to claim 1.

* * * * *

UNITED STATES PATENT AND TRADEMARK OFFICE
CERTIFICATE OF CORRECTION

PATENT NO.      : 6,312,718 B1
DATED           : November 6, 2001
INVENTOR(S)     : Mircea C. Popescu et al.

It is certified that error appears in the above-identified patent and that said Letters Patent is hereby corrected as shown below:

<u>Column 12,</u>
Line 67, replace "cytoldne" with -- cytokine --.

<u>Column 13,</u>
Line 6, replace "contains anidotype" with -- containing an idiotype --.

Signed and Sealed this

Twenty-eighth Day of October, 2003

JAMES E. ROGAN
*Director of the United States Patent and Trademark Office*